US006760112B2

(12) United States Patent
Reed et al.

(10) Patent No.: US 6,760,112 B2
(45) Date of Patent: Jul. 6, 2004

(54) GRIN-FIBER LENS BASED OPTICAL ENDOSCOPES

(75) Inventors: William Alfred Reed, Summit, NJ (US); Mark J Schnitzer, Summit, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 150 days.

(21) Appl. No.: 09/919,017

(22) Filed: Jul. 31, 2001

(65) Prior Publication Data

US 2002/0141714 A1 Oct. 3, 2002

Related U.S. Application Data

(60) Provisional application No. 60/269,586, filed on Feb. 17, 2001.

(51) Int. Cl.[7] .............................. G01B 9/02; G02B 6/32
(52) U.S. Cl. ........................................ 356/477; 385/34
(58) Field of Search ....................... 356/477; 250/227.2, 250/227.29, 227.26, 227.27, 227.19, 216; 385/34

(56) References Cited

U.S. PATENT DOCUMENTS

| | | | |
|---|---|---|---|
| 4,217,027 A | | 8/1980 | MacChesney et al. |
| 4,262,035 A | | 4/1981 | Jaeger et al. |
| 4,701,011 A | | 10/1987 | Emkey et al. |
| 4,900,120 A | | 2/1990 | Caviglia et al. |
| 4,909,816 A | | 3/1990 | MacChesney et al. |

(List continued on next page.)

FOREIGN PATENT DOCUMENTS

| | | |
|---|---|---|
| DE | 512393 | 6/1994 |
| EP | 0972752 A1 | 1/2000 |
| EP | 1035083 A1 | 9/2000 |
| WO | WO 01/11409 A2 | 2/2001 |

OTHER PUBLICATIONS

Patent Abstracts of Japan Publication No. 60166244, "Manufacture of Optical Fiber Preform" by Okamura Koji (Published on Aug. 29, 1985, by Japanese Patent Office) 1 pg.
Emkey, W. L. et al: "Analysis and Evaluation of Graded–Index Fiber–Lenses" Journal of Lightwave Technology, vol. LT–5, No. 9, Sep. 9, 1987, pp. 1156–1164.
Shiraishi, K. et al: "Spotsize Contraction in Standard Single–Mode Fibers by Use of a Gl–Fiber Tip with a High Focusing Parameter" IEEE Photonics Technology Letters, vol. 10, No. 12, Dec. 1998, pp. 1757–1759.
U.S. patent application Ser. No. 09/896,777, Reed et al., filed Jun. 29, 2001.
U.S. patent application Ser. No. 09/896,789, Reed et al., filed Jun. 29, 2001.
U.S. patent application Ser. No. 09/922,659, Fee et al., filed Aug. 6, 2001.
Emkey, W.L. et al., *IEEE*, "Analysis and Evaluation of Graded–Index Fiber–Lenses", vol. 5, No. 9, pp. 1156–1164, Sep. 1987.
Chanclou, P. et al., "Expanded Single Mode Fiber", WDD4, 2000, 3 pages.
A Product Announcement of ENS Bretagne, Chanclou, P. et al., "Expanded Signel Mode Fiber", 1–page, Mar. 2001.

*Primary Examiner*—Samuel A. Turner
*Assistant Examiner*—Patrick J Connolly
(74) *Attorney, Agent, or Firm*—John F. McCabe

(57) ABSTRACT

An optical system for monitoring or imaging a sample includes a probe, an optical splitter or circulator, and an optical detector. The probe includes an optical fiber and a GRIN fiber-size lens fused to one end of the fiber. The optical splitter or circulator receives light from a source and directs a portion of the received light to the fiber. The optical detector is coupled to receive a portion of light collected from the sample by the GRIN fiber-size lens and is configured determine a characteristic of the sample from the received light.

17 Claims, 5 Drawing Sheets

U.S. PATENT DOCUMENTS

| | | |
|---|---|---|
| 5,050,954 A | 9/1991 | Gardner et al. |
| 5,076,672 A | 12/1991 | Tsuda et al. |
| 5,321,501 A | 6/1994 | Swanson |
| 5,337,380 A | 8/1994 | Darbon et al. |
| 5,384,874 A | 1/1995 | Hirai et al. |
| 5,680,237 A | 10/1997 | Cheng |
| 5,881,195 A * | 3/1999 | Walker ....................... 385/116 |
| 5,905,838 A | 5/1999 | Judy et al. |
| 5,910,839 A | 6/1999 | Erskine |
| 5,956,355 A | 9/1999 | Swanson |
| 6,014,483 A | 1/2000 | Thual et al. |
| 6,105,396 A | 8/2000 | Glodis et al. |
| 6,131,413 A | 10/2000 | Rousseau et al. |
| 6,134,003 A * | 10/2000 | Tearney et al. ............. 356/450 |
| 6,172,817 B1 | 1/2001 | Senapati et al. |
| 6,219,477 B1 | 4/2001 | Peck, Jr. |
| 6,445,939 B1 * | 9/2002 | Swanson et al. .............. 385/34 |

* cited by examiner

GRIN-FIBER LENS BASED OPTICAL ENDOSCOPES

This application claims the benefit of U.S. Provisional Application No. 60/269,586, filed Feb. 17, 2001.

BACKGROUND OF THE INVENTION

1. Field of the Invention

This invention relates to optical endoscopes and imaging systems.

2. Discussion of the Related Art

Contemporary medical technology uses x-rays, sound waves, and visible light to produce in vivo images of biological tissues. Visible light and infrared (IR) imaging has better potential resolution than is obtainable with sound waves, because visible light and IR light have shorter wavelengths than sound waves. In spite of this advantage, some in vivo imaging systems use sound waves, because visible and IR light does not penetrate thick tissues. Consequently, many in vivo imaging systems do not have the image resolution obtainable in systems based on visible or IR light.

One method that enables using visible and IR light in medical imaging entails the use of endoscopes that are inserted into the body being imaged. Present medical technology uses endoscopes in both non-invasive and invasive techniques. In the non-invasive techniques, the endoscope is inserted into hollow body structures such as arteries, veins, and the digestive tract. In the invasive technique, the endoscope is inserted into interiors of solid body tissues. Unlike the non-invasive techniques, invasive endoscopy typically produces some tissue damage during insertion of the endoscope. The tissue damage is particularly undesirable in sensitive organs such as the brain. Such tissue damage has limited the use of invasive endoscopy and of optical techniques for imaging interiors of solid tissues.

BRIEF SUMMARY OF THE INVENTION

Various embodiments provide optical micro-probes for use in imaging and monitoring. The optical micro-probes can have smaller diameters than conventional endoscopes. Exemplary optical micro-probes have diameters of 0.127 millimeters (mm) as compared to a typical endoscope diameter of about 0.5 mm to 4 mm. The smaller diameters enable inserting the new optical micro-probes into body tissues via narrow needles, e.g., 31 gauge needles, which reduces tissue damage during invasive endoscopy.

One embodiment according to principles of the invention features an optical system for monitoring or imaging a sample. The system includes an optical micro-probe, an optical splitter or circulator, and an optical detector. The optical micro-probe includes an optical fiber and a graded refractive index (GRIN) fiber-size lens fused to one end of the fiber. The optical splitter or circulator receives light from a source and directs a portion of the received light to the optical fiber. The optical detector is coupled to receive a portion of light collected from the sample by the GRIN fiber-size lens and is configured determine a characteristic of the sample from the received light.

DETAILED DESCRIPTION OF THE EMBODIMENTS

1. Optical Micro-Probe and Imaging System

Figure 1A:
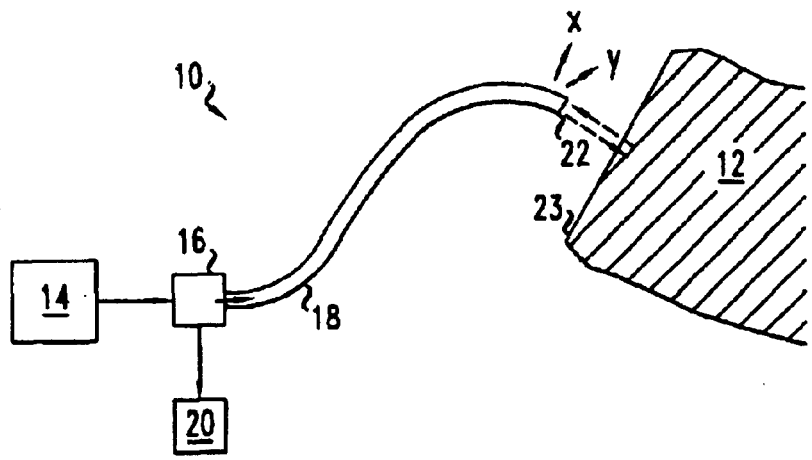
FIG. 1A shows a system that optically monitors or images a sample.

FIG. 1A shows a system 10 for optically monitoring or imaging a region of a sample 12, e.g., for endoscopic viewing of a biological tissue. Various embodiments of the system 10 determine the velocity and/or three-dimensional position of the region being monitored or imaged, e.g., via tomography. Such monitoring or imaging functions are useful for medical diagnostics and treatment, e.g., invasive imaging of anomalous tissue structures in vivo and monitoring of tissue motion during other medical procedures.

The system 10 includes a source 14 of IR, visible, or ultraviolet light, an optical splitter or circulator 16, an optical micro-probe 18, and a light detector 20. Exemplary sources 12 include monochromatic sources or multichromatic sources, e.g., a pulsed Ti-sapphire laser with a low coherence time of about $10^{-15}$–$10^{-13}$ seconds. The optical splitter or circulator 16 directs a portion of the light from the source 14 to the optical micro-probe 18. The optical micro-probe 18 has a distal end 22 located either above or below the surface 23 of the remote sample 12. The optical micro-probe 18 delivers the source light to a region of the sample 12. The optical micro-probe 18 also returns to the splitter or circulator 16 a portion of the light scattered or emitted by the region of the sample 12 illuminated by the optical micro-probe 18. The optical splitter or circulator 16 redirects the returned light to detector 20. The detector 20 uses the returned light to determine a scattering or emission characteristic of the region of the sample 12 that produced the light. Some detectors 20 are configured to determine the distance of the region from the optical micro-probe 18 and/or the velocity of the region.

Figure 2:
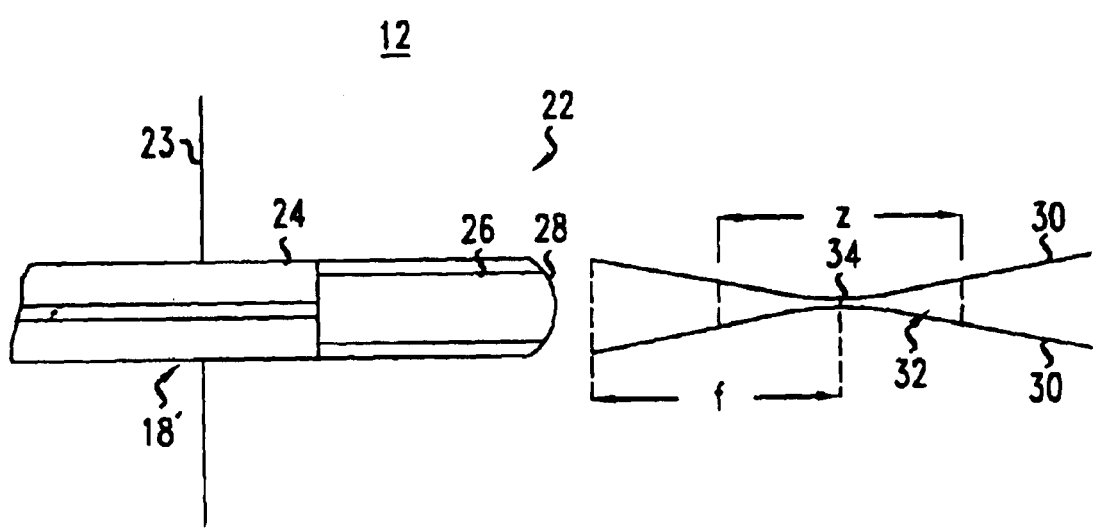
FIG. 2 shows a graded index (GRIN) fiber-size lens used in some embodiments of the probe of FIG. 1A.

FIG. 2 shows one embodiment 18' of optical micro-probe 18 shown in FIG. 1A. The optical micro-probe 18' includes a single-mode optical fiber 24 that transports light to and from the sample 12. The distal end 22 of the fiber 24 is fused to a GRIN fiber-size lens 26, which has the same outer diameter as the optical fiber 24. In some embodiments, the GRIN fiber-size lens 26 also has a rounded end face 28 that facilitates insertion of the end 22 of the optical micro-probe 18' into samples such as biological tissues. In some embodiments, a portion of the GRIN fiber-size lens 26 adjacent the end face 28 has a conical taper (not shown). The taper also facilitates insertion of the optical micro-probe 18 into sample 12, i.e., the taper functions like a needle's point.

The GRIN fiber-size lens 26 collimates light from fiber 24 into a collimated beam 30. The collimated beam 30 illuminates a region of the sample 12 located forward of the lens 26. Points 32 in the illuminated region scatter or emit light in response to being illuminated. The backscattered or emitted light is useable for imaging or monitoring. The beam collimation enables resolving transverse locations of the points 32 with respect to the axis of the GRIN fiber-sized lens 26, because points 32 producing backscattered or emitted light are located within the region illuminated by the beam 30.

In some embodiments, a mechanical driver (not shown) drives the distal end 22 of optical micro-probe 18 to execute scanning motions parallel and/or transverse to the axis of the GRIN fiber-size lens 26. These scanning motions enable system 10 to collect optical data for two-dimensional or three-dimensional images of the sample 12, i.e., i.e., a planar or full 3D image.

Illumination beam 30 has a width that varies with distance from the end surface 28 of the GRIN fiber-size lens 26. The beam width has a minimum value at an approximate focal point 34 of the GRIN fiber-size lens 26, i.e., at a distance "f" from end face 28. Typically, the distance "f" has a value from about 0.2 millimeters (mm) to about 1.5 mm, and exemplary values of "f" are greater than about 0.8 mm. The beam 30 has a divergence that is characterized by a rayleigh range "z". Herein, the rayleigh range is half the length of the portion of the beam 30 that has a width less than about √2 times the minimum width at the approximate focal point 34. An exemplary GRIN fiber-size lens 26 has a rayleigh range greater than about 200 microns ($\mu$), e.g., $z \geq 300\mu$ or 8 mm $\geq z \geq 300\mu$.

The focal distance and rayleigh range of GRIN fiber-size lens 26 depend on the radial profile of the refractive index in the GRIN lens and on the length of the GRIN lens. GRIN fiber-size lens 26 is either a conventional GRIN fiber-size lens or a new GRIN fiber-size lens with a gentler refractive index profile.

Figure 3A:
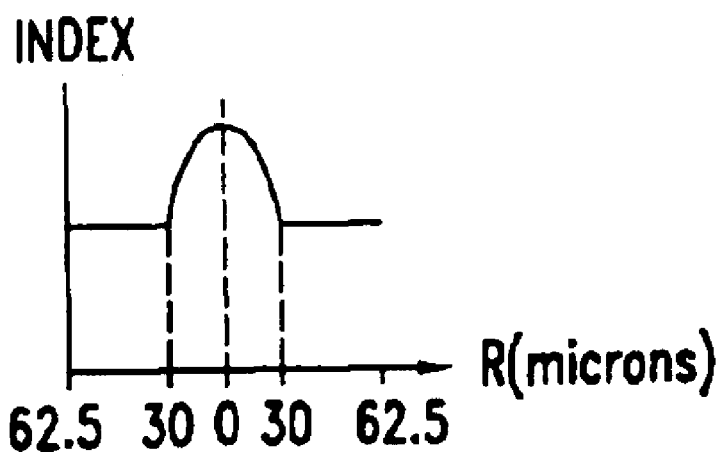
FIG. 3A shows a conventional GRIN fiber lens.

Conventional GRIN fiber lenses are described in U.S. Pat. No. 4,701,011, which is incorporated herein by reference in its entirety. FIG. 3A shows the radial refractive index profile of one such GRIN fiber lens. The refractive index is constant over a range of values of the radius that correspond to the fiber's outer cladding and varies over values of the radius that correspond to the fiber's core. Restricting the refractive index variations to the core typically produces a GRIN fiber lens with a short focal length, less than about 0.7 mm, and a short rayleigh range, e.g., less than $200\mu$.

Figure 3B:
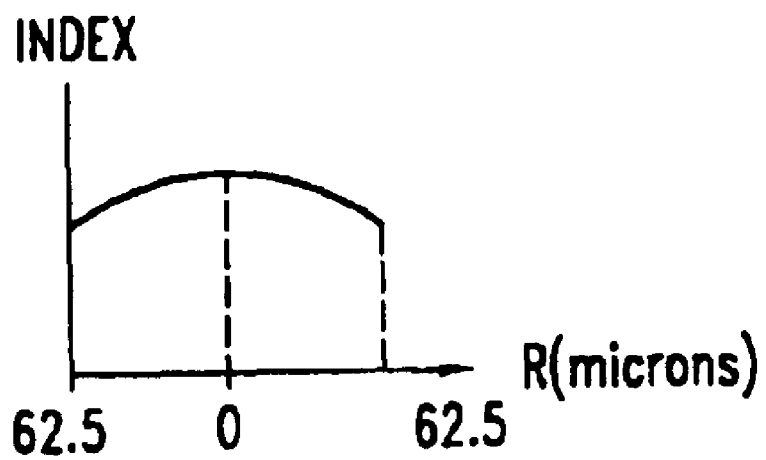
FIG. 3B shows a refractive index profile for one embodiment of the GRIN fiber-size lens of FIG. 2.

FIG. 3B shows a radial refractive index profile of a new GRIN fiber-size lens 26 for which the profile's radial curvature is smaller in magnitude than in conventional GRIN fiber-size lenses. The smaller magnitude curvature causes the new GRIN fiber-size lens to have a longer focal length than the conventional GRIN fiber lens associated with the profile of FIG. 3A. The new GRIN fiber-size lenses are described in co-pending U.S. patent application Ser. No. 09/896,789, filed Jun. 29, 2001, which is incorporated herein by reference in its entirety.

In the profile of FIG. 3B, the refractive index varies over the whole diameter of the lens. Thus, the new GRIN fiber-size lens has no outer cladding. The absence of cladding increases the radial range over which the refractive index varies, which results in the associated GRIN fiber-size lens having a longer rayleigh range than the GRIN fiber-size lens associated with the profile FIG. 3A.

Refractive index profiles are characterized by a parameter "g" that measures the radial curvature of the profile in the core of a GRIN fiber lens. In particular, the parameter g is defined as:

$$g = -\frac{1}{n_0} \frac{d^2 P(r)}{dr^2}\bigg|_{r=0}$$

Here, "r" is radial distance for the axis of the GRIN fiber lens, $n_0$ is the value of the refractive index on the axis of the GRIN fiber lens, and P(r) is the value of the refractive index at the distance "r" from the axis of the fiber lens.

Exemplary new GRIN fiber-size lenses have refractive index profiles whose radial curvatures are smaller in magnitude than those disclosed in Table 1 of "Analysis and Evaluation of Graded-Index Fiber-Lenses", Journal of Lightwave Technology, Vol. LT-5, No. 9 (September 1987), pages 1156–1164, by W. L. Emkey et al, which is incorporated by reference herein in its entirety. The new GRIN fiber-size lenses 26 have a "g" that is less than $1.7 \times 10^{-6}$ $\mu m^{-2}$, preferable less than about $0.9 \times 10^{-6}$ $\mu m^{-2}$ and more preferably less than about $5.0 \times 10^{-7}$ $\mu m^{-2}$. For 125 $\mu m$—diameter GRIN fiber lenses 18, values of "g" are selected from the range $1.7 \times 10^{-6}$ $\mu m^{-2}$ to $5.0 \times 10^{-7}$ $\mu m^{-2}$ and preferably in the range $0.9 \times 10^{-6}$ $\mu m^{-2}$ to $5.0 \times 10^{-7}$ $\mu m^{-2}$ to provide good beam collimation.

Referring again to FIG. 2, the above-disclosed refractive index profiles produce focal lengths and rayleigh ranges for GRIN fiber-size lens 26 that are consistent with the above-recited values. Some embodiments of optical micro-probe 18' use a GRIN fiber-size lens 26 with a profile similar to that of FIG. 3B, because such a profile provides a longer rayleigh range. The longer rayleigh range provides a larger usable depth range for sample probing. Typically, the usable depth of the optical micro-probe 18' is about 1 to 8 rayleigh ranges from the focal point 34.

Figure 1B:
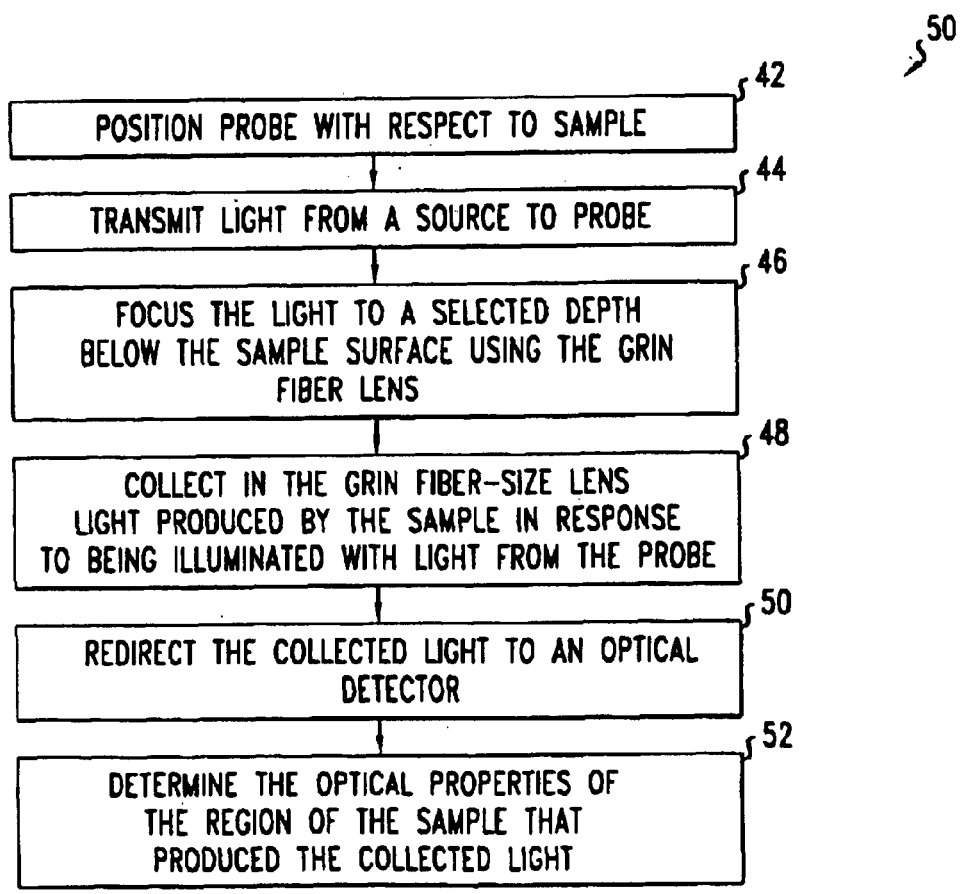
FIG. 1B is a flow chart for a process that uses the system of FIG. 1A.

FIG. 1B is a flow chart for a process 40 that uses system 10 of FIGS. 1A and 2. The process 40 includes positioning distal end 22 of the optical micro-probe to monitor a selected portion of sample 12 (step 42). The positioning includes selecting an orientation of the optical micro-probe 18 with respect to the sample surface 23 and selecting a lateral position and depth for the distal end 22 with respect to the sample surface 23. After positioning the optical micro-probe 18, source 14 transmits source light to the optical micro-probe 18 via splitter or circulator 16 (step 44). The transmitted source light passes through GRIN fiber-size lens 26, which focuses the light into beam 30 (step 46). The region illuminated by the beam 30 produces the scattered or emitted light. The GRIN fiber-size lens 26 collects a portion of the light that is scattered or emitted by the illuminated region of the sample (step 48). The optical micro-probe 18 returns the light collected by the GRIN fiber-size lens 26 to the optical splitter or circulator 16, which redirects a portion of the returned light to optical detector 20 (step 50). The detector 20 determines the scattering or emission characteristics of the region of the sample 12 from the light redirected thereto (step 52). Since the beam 30 has an intensity that varies with the beam width, the detector 20 primarily receives light from a region of the sample 12 that has a volume limited by the boundary of the beam 30. The volume includes sample points within about 1 to 8 rayleigh ranges of focal point 34. The light from the sample points and known position and orientation of optical micro-probe 18 enable using data from detector 20 to determine lateral positions and depths of the sample points backscattering or emitting light in some embodiments of system 10.

2. Interferometric Optical Monitoring and Imaging

Figure 4A:
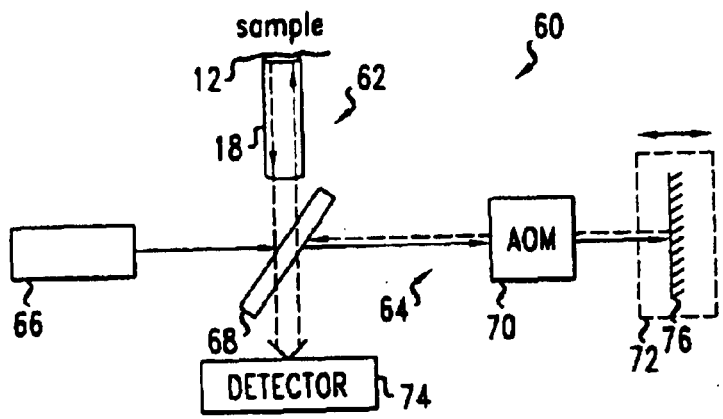
FIGS. 4A and 4B show embodiments of the system of FIG. 1A that incorporate optical interferometers.
Figure 4B:
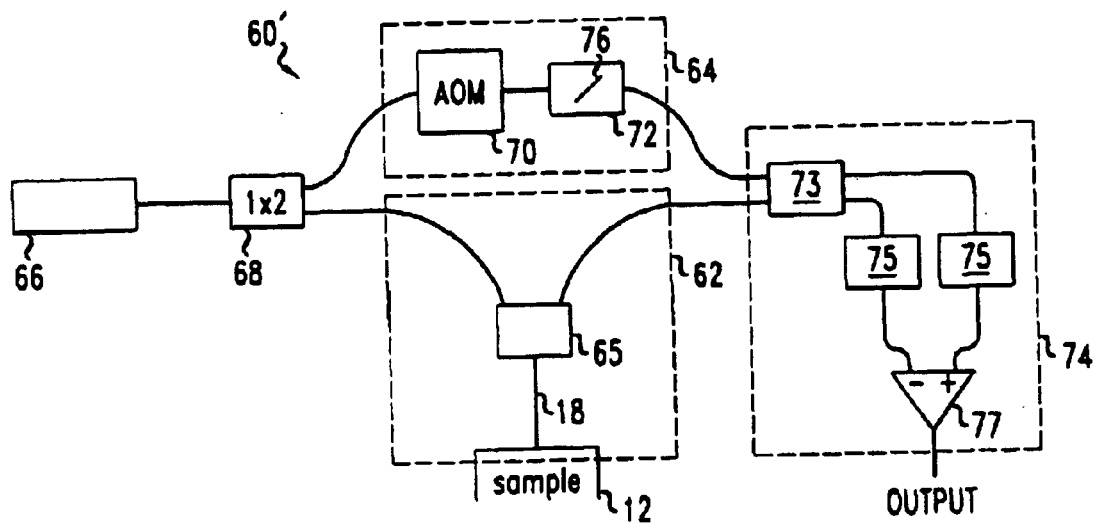

A co-pending patent application describes monitoring and imagining systems that determine depth and/or velocity information for a region of a sample that scatters or emits light in response to being illuminated by an optical micro-probe. Exemplary optical micro-probes include probe 18' with attached GRIN fiber-sized lens 26, as shown in FIG. 2, and single mode optical fibers without attached terminal GRIN fiber-sized lenses. FIGS. 4A and 4B show two such embodiments 60, 60'. To determine depths, the systems 60, 60' use "low-coherence interferometry" a method known to those of skill in the art.

Each system 60, 60' includes an interferometer with a measurement arm 62 and a reference arm 64. The two arms 62, 64 receive light from a multi-chromatic source 66, i.e., a low-temporal coherence source. Typically, source 66 is spatially coherent. The measurement arm 62 outputs light scattered by sample points in response to being illuminated by source light.

Each system 60, 60' interferometrically combines the light outputted by measurement arm 62 and reference arm 64. The combined light provides an output signal sensitive to optical path differences between the two arms 62, 64 because of the low-coherence nature of source 66. Interferometric combining of light requires that the difference in the optical path lengths traversed by the light being combined, e.g., the path difference between the two arms 62, 64, be less than the light's coherence length, e.g., the coherence length of the source 66. Interference detector 74 uses the interferometrically combined light to determine one or more characteristics of the region of the sample 12 that produced scattered light, e.g., the intensity of the light scattered back into the optical micro-probe 18. Thus, the sensitivity to optical path differences makes detector 74 sensitive to the depth of sample points 32 producing scattered light. The detector 74 is only sensitive to light produced by sample points 32 that are located within the sample depth range for which the optical path length difference between the measurement and reference arms 62, 64 is less than the coherence length of the source 66.

To increase depth resolution, a less coherent source 66, e.g., a pulsed Ti-sapphire laser, is used in systems 60, 60'. The source 66 has a coherence length that is at least less than one centimeter and typically is less than one millimeter. In some embodiments, the source 66 has a coherence length that is as small as 100 microns or even 1 micron. Since interferometric combination only occurs if some optical path length differences between the measurement and reference arms 62, 64 are less than about one coherence length, this condition defines the depth resolution of the system 10. For a sample depth resolution of 10 microns, the source 14 should produce an output beam that is only coherent for a time equal to about $10^{-5}$ meters/$\{3 \times 10^8$ meters/second$\} = 3 \times 10^{-14}$ seconds.

The systems 60 and 60' of FIGS. 4A and 4B include a Michelson interferometer and a Mach-Zehnder interferometer, respectively. Each system 60, 60' has an optical splitter/combiner 68 that couples to one end of the measurement and reference arms 62, 64. The optical splitter/combiner 68 transmits mutually coherent light from low-coherence source 66 to the measurement and reference arms 62, 64. The measurement arm 62 includes optical micro-probe 18. In the system 60' of FIG. 4B, the probe 18 connects to the measurement arm 62 through an optical circulator 65. The probe 18 illuminates a sample region with source light and also collects light scattered produced by the illuminated sample region. In some embodiments, the optical micro-probe is a single-mode fiber 24 having a GRIN fiber-size lens 26 fused to its distal end 22. The reference arm 64 includes a moveable reflector 76, e.g. a moving mirror, and an acousto-optical modulator (AOM) 70. The moveable reflector allows an operator to change the optical path length of the reference arm 64, i.e., to scan different sample depths by moving the reflector 76. The AOM 70 acoustically frequency shifts the source light received from the splitter/combiner 68 and enables velocities of sample points 34 to be measured (see below). Some embodiments include dispersion compensator 72 that corrects differences in chromatic dispersion or pulse broadening between light propagating in the measurement and reference arms 62, 64. The construction of dispersion compensators is known to those of skill in the art.

The interference detector 74 receives frequency-shifted light from the reference arm 64 and light scattered by the sample from the measurement arm 62. The arms 62, 64 have optical path lengths that are equal to within about one coherence length of source 66 so that some light from the two arms 62, 64 interferometrically combines in the detector 74, i.e., light produced by scattering at some sample depth. The detector 74 determines characteristics of regions of the sample producing light that interferometrically combines with light from the reference arm 64. The moving reflector 76 enables an operator to adjust the optical path length difference between the reference and measurement arms 64, 62 so that sample depths can be scanned by the interference detector 74. Through such scans, the systems 60, 60' are able to generate images of the sample 12 as a function of sample depth.

FIG. 4B also shows an exemplary interference detector 74. The exemplary interference detector 74 includes a 50/50 optical splitter/combiner 73 that produces signals with a 180° phase difference on its two output terminals. From the 50/50 optical splitter/combiner 73, the 180° out of phase optical signals go to separate intensity detectors 75. Outputs of the intensity detectors 73 couple to the inputs of a differential amplifier 77 whose output signal is representative of optical interference between signals from the reference and measurement arms 64, 62.

Figure 4C:
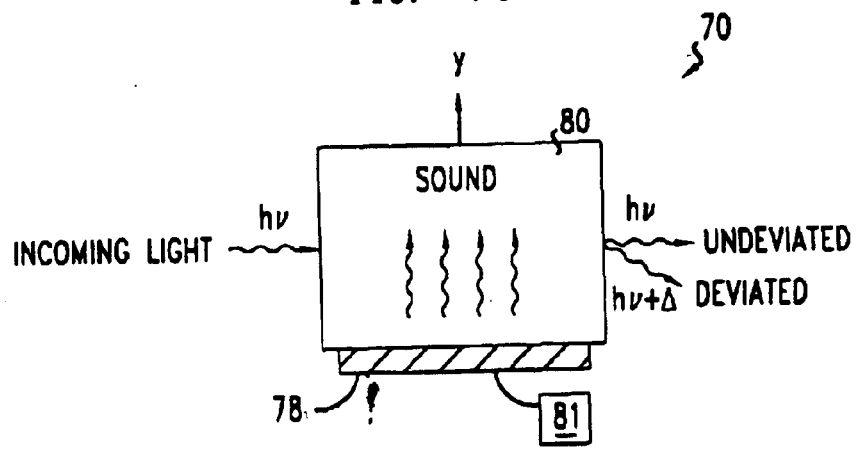
FIG. 4C illustrates an acousto-optical modulator used in the interferometers of FIGS. 4A and 4B.

Referring to FIG. 4C, AOM 70 includes a radio frequency (RF) source 78 and an optical medium 80. The RF source 78 excites sound waves, i.e., phonons, in the optical medium 80. The sound waves are directed along direction "Y" and have the source's RF frequency. A voltage oscillator 81 drives the RF source 78. In some embodiments, the oscillator 81 is variable so that the phonon frequency is variable.

Referring to FIGS. 4A–4C, a photon in reference arm 64 may absorb or emit a phonon while propagating through the optical medium 80. Absorption or emission of a phonon produces both a frequency-shift, i.e., $\pm \Delta/h$, and a direction-change for the photon. Thus, the acoustically-driven medium 80 produces both directionally undeviated output light, i.e., photons that have neither absorbed nor emitted a phonon, and directionally deviated output light, i.e., photons that have absorbed or emitted a phonon. Momentum conservation fixes the directions of the deviated output light to be different from the direction of the undeviated output light. The AOM 70 is configured to deliver deviated output light of one frequency to the detector 74 and to not deliver the undeviated output light to the detector 74. One embodiment screens out the undeviated light by imaging only deviated light, which has a new propagation direction, on an optical fiber that delivers light to moving reflector 72. Thus, the interference detector 74 receives light whose frequency has been shifted by absorption or emission of a phonon in the AOM 70.

In some embodiments, the light makes two passes through the AOM 70, and the AOM 70 screens out light whose frequency has not been shifted by the absorption or emission of two phonons. Then, this AOM 70 produces light whose frequency is shifted with respect to the optical source 66 by twice the frequency of the RF source 78.

Referring again to FIGS. 4A–4B, the detector 74 obtains information on the displacement or velocity of the region of the sample 12 that backscatters source. The displacement or velocity information is encoded in the size of the Doppler shift caused by the velocity of the scattering region of the sample 12. The AOM 70 enables detection of such Doppler shifts through phase-sensitive detection, which are known to those of skill in the art. In some embodiments, this detection technique enables a determination of both the sign and the magnitude of the velocities of scattering sample particles along the axis of optical micro-probe 18. In other embodiments, this detection technique enables a determination of both the sign and the magnitude of displacements of scattering sample particles along the axis of optical micro-probe 18.

The AOM 70 provides light outputted by the reference arm 64 with a different frequency from the frequency of light outputted by the measurement arm 62. In the absence of sample motion, this frequency difference is equal to the frequency of the RF energy driving the AOM 70, i.e., if the reference arm 64 produces photons that absorb or emit one phonon. Sample motion at the depth for which the path difference between the measurement and reference arms 62, 64 vanishes changes the frequency difference between the light from the two arms 62, 64, i.e., due to Doppler shifting. The detector 74 uses the magnitude of the change in the frequency difference between the light from the two arms 62, 64 to determine the speed of a sample particle producing scattering. The detector 74 uses the phase of the change in frequency difference, i.e., positive or negative, to determine the sign of the sample motion, i.e., towards or away from the optical micro-probe 18. Standard electronic or optical techniques are known for determining both the magnitude and sign of the frequency difference between the light from the two arms 62, 64.

The systems 60, 60' use the AOM 70 to determine information representative of velocities of sample points at a selected sample depth. Information representative of velocities of sample points includes signed displacements and velocities of the sample points along the axis of probe 18. The systems 60, 60' are also able to select different optical path lengths for the reference arm 64, i.e., by moving reflector 76. By scanning such optical path lengths, systems 60, 60' are able to select different sample depths for which interferometric combination of scattered light from the measurement arm 62 and light from the reference arm 64 occurs. During such a scan, detector 74 determines sample region velocities as a function of distance from end 22 of optical micro-probe 18, i.e., as a function of sample depth. This type of scan of sample velocities as a function of depth enables, e.g., for mapping blood flow rates in an artery of an animal or patient.

The AOM 70 shifts light in the reference arm 64 by a single frequency. This simple form of the frequency shift enables the detector 74 to determine velocities in the sample 12.

Figure 5:
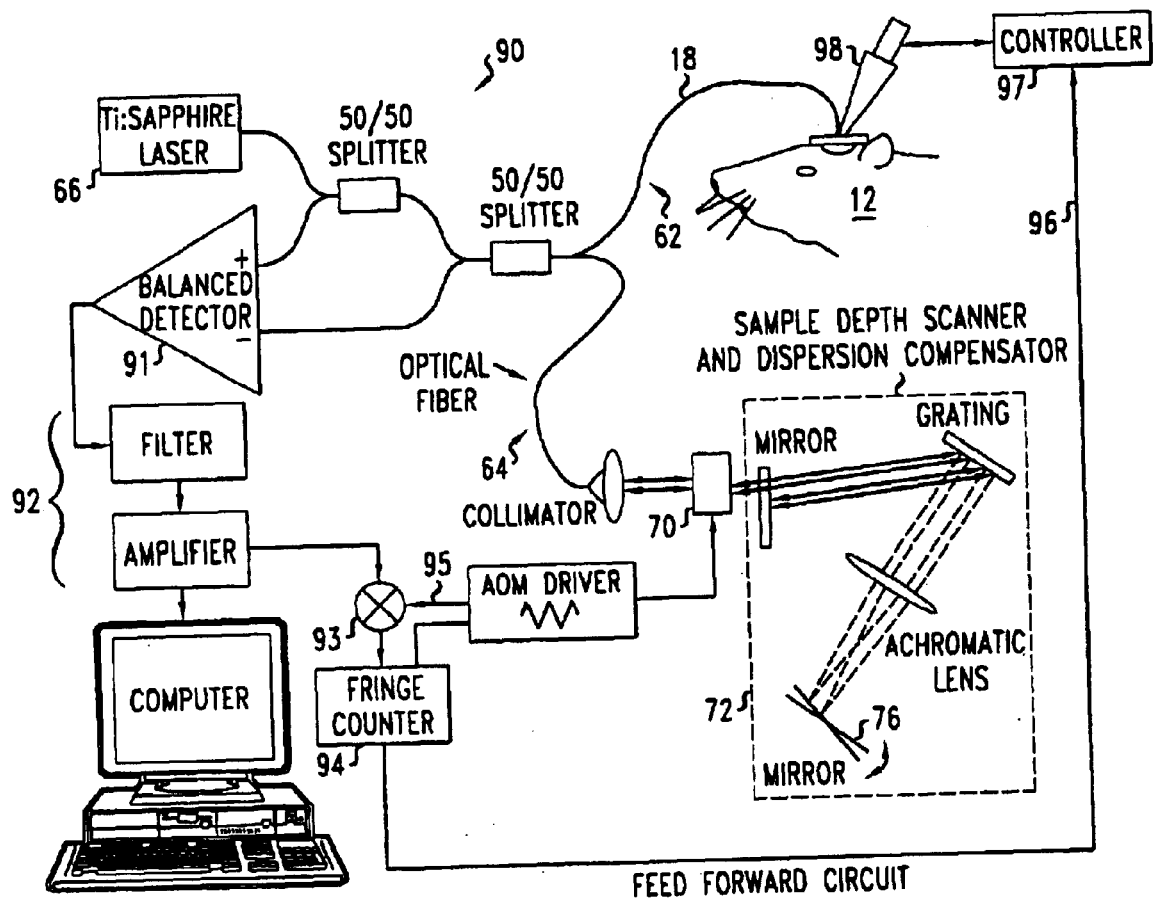
FIG. 5 shows a medical diagnostic system based on the system of FIGS. 4A and 4C.

FIG. 5 shows a medical diagnostic system 90 based on system 60 of FIGS. 4A and 4C. The system 90 includes a differential amplifier 91 and an electronic filtering chain 92 that amplify and remove input noise, respectively. The system 90 also includes a multiplier 93 that combines a signal representative of the interferometrically combined optical signals from the measurement and reference arms 62, 64 with a signal representative of the RF signal driving RF source 78. The output of the multiplier 93 goes to a fringe counter 94 that determines both the magnitude and sign of the velocity of a monitored portion of the sample. To determine the sign of the velocity, i.e., towards or away from optical micro-probe 18, the counter 94 compares the signal from the multiplier 93 when the multiplier receives, i.e., via line 95, different signals representative of the RF signal driving source 78. The different signals are out of phase by 90°.

The fringe counter 94 couples to a feed forward circuit 96 that in turn transmits information on the velocity and/or position of sample 12 to a controller 97. The controller 97 is connected to a second diagnostic probe 98, e.g., a monitoring electrode or a scanner for the same sample 12. The controller 97 uses the information fed forward by circuit 96 to correct data that is output by the probe 98 for the effects of sample motion. In some embodiments, the controller 97 mechanically adjusts the position of the second diagnostic probe 98 to eliminate relative motion between the sample and probe 98. In other embodiments, the controller 97 corrects the data collected by the second diagnostic probe 98 to compensate for the motion of the sample 12, e.g., by displacing image scan data to eliminate motion induced smearing.

Other embodiments of the invention will be apparent to those skilled in the art in light of the specification, drawings, and claims of this application.

What is claimed is:

1. An optical system for monitoring or imaging a sample, comprising:

a probe having an optical fiber and a GRIN fiber-size lens fused to one end of the fiber;

an optical splitter or circulator to receive light from a source and to direct a portion of the received light to the fiber; and an optical detector coupled to receive a portion of light collected from the sample by the GRIN fiber-size lens and to determine a characteristic of the sample from the received light; and wherein the GRIN fiber-size lens has a rayleigh range that is greater than 200 microns.

2. The system of claim 1, wherein the GRIN fiber-size lens has a focal length of greater than 1 mm.

3. The system of claim 1, wherein the GRIN fiber-size lens has a rayleigh range of at least 500 microns.

4. The optical system of claim 1
   wherein the GRIN fiber-size lens does not have an integral outer optical cladding layer.

5. The system of claim 1, wherein a free end-face of the GRIN fiber-size lens is convexly rounded.

6. The system of claim 1, wherein the monitoring system comprises an optical interferometer having measurement and reference arms, both arms being optically coupled to receive light from the splitter or circulator, the measurement arm including the probe.

7. The system of claim 6, further comprising:

an optical source coupled to transmit light to the measurement and reference arms and capable of producing light with a coherence length of less than 1 centimeter.

8. The system of claim 7, wherein one of the reference arm and the measurement arm has a variable optical path length.

9. A process for optically monitoring or imaging a sample, comprising:

directing light into an optical fiber;

directing light from the fiber into a portion of the sample with a GRIN fiber-size lens that has a rayleigh range that is greater than 200 microns;

receiving light in the GRIN fiber-size lens in response to the received light being scattering or emitted by a region of the sample; and transmitting the received light to a detector.

10. The process of claim 9, further comprising:

determining one of a density, a depth, and a velocity of the portion of the sample based on the received light.

11. The process of claim 10, further comprising:
producing an image of the sample with data determined by the detector.

12. The process of claim 10, wherein the GRIN fiber-size lens has a focal length of greater than 1 mm.

13. An optical system for monitoring or imaging a sample, comprising:
a probe having an optical fiber and a GRIN fiber-size lens fused to one end of the fiber, the end having an optical core and an optical cladding;
an optical splitter or circulator to receive light from a source and to direct a portion of the received light to the fiber; and
an optical detector coupled to receive a portion of light collected from the sample by the GRIN fiber-size lens and to determine a characteristic of the sample from the received light; and
wherein the GRIN fiber-size lens has a focal length of greater than 1 mm.

14. The system of claim 13, wherein the GRIN fiber-size lens does not have an integral outer optical cladding layer.

15. The system of claim 13, wherein a free end-face of the GRIN fiber-size lens is convexly rounded.

16. The system of claim 13, wherein the monitoring system comprises an optical interferometer having a measurement and reference arms, both arms being optically coupled to receive light from the splitter or circulator, the measurement arm including the probe.

17. The system of claim 13, wherein one of the reference arm and the measurement arm has a variable optical path length.

* * * * *